(12) United States Patent
Edelson

(10) Patent No.: US 9,649,266 B2
(45) Date of Patent: May 16, 2017

(54) METHODS TO TREAT, PREVENT, AND IMPROVE SKIN CONDITIONS

(71) Applicant: Anterios, Inc., New York, NY (US)

(72) Inventor: Jonathan Edelson, Scarsdale, NY (US)

(73) Assignee: Anterios, Inc., New York, NY (US)

( * ) Notice: Subject to any disclaimer, the term of this patent is extended or adjusted under 35 U.S.C. 154(b) by 0 days.

(21) Appl. No.: 14/702,256

(22) Filed: May 1, 2015

(65) Prior Publication Data
US 2015/0313819 A1 Nov. 5, 2015

Related U.S. Application Data

(60) Provisional application No. 61/987,103, filed on May 1, 2014.

(51) Int. Cl.
| | |
|---|---|
| *A61K 8/41* | (2006.01) |
| *A61K 31/49* | (2006.01) |
| *A61K 31/4188* | (2006.01) |
| *A61K 31/435* | (2006.01) |
| *A61Q 19/00* | (2006.01) |
| *A61K 8/49* | (2006.01) |
| *A61K 31/13* | (2006.01) |
| *A61K 31/4453* | (2006.01) |
| *A61K 9/14* | (2006.01) |
| *A61K 9/19* | (2006.01) |

(52) U.S. Cl.
CPC ............. *A61K 8/41* (2013.01); *A61K 8/49* (2013.01); *A61K 8/4926* (2013.01); *A61K 9/143* (2013.01); *A61K 9/145* (2013.01); *A61K 9/19* (2013.01); *A61K 31/13* (2013.01); *A61K 31/4188* (2013.01); *A61K 31/435* (2013.01); *A61K 31/4453* (2013.01); *A61Q 19/00* (2013.01); *A61Q 19/008* (2013.01); *A61K 2800/782* (2013.01)

(58) Field of Classification Search
IPC ..................... A61K 8/41,8/49, 31/4188, 31/435
See application file for complete search history.

(56) References Cited

U.S. PATENT DOCUMENTS

| | | | |
|---|---|---|---|
| 5,008,110 A | 4/1991 | Benecke et al. | |
| 5,591,767 A | 1/1997 | Mohr et al. | |
| 5,683,712 A | 11/1997 | Cavazza | |
| 5,948,433 A | 9/1999 | Burton et al. | |
| 5,965,154 A | 10/1999 | Haralambopoulos | |
| 6,010,715 A | 1/2000 | Wick et al. | |
| 6,469,227 B1 * | 10/2002 | Cooke | A61K 9/70 424/443 |
| 7,226,605 B2 | 6/2007 | Suskind et al. | |
| 7,288,259 B2 | 10/2007 | Sanders et al. | |
| 7,939,567 B2 * | 5/2011 | Wu | A61K 31/485 514/656 |
| 8,153,139 B1 | 4/2012 | Sanders et al. | |
| 2007/0203164 A1 | 8/2007 | Chiang et al. | |
| 2007/0287733 A1 | 12/2007 | Snorrason | |

FOREIGN PATENT DOCUMENTS

| | | | |
|---|---|---|---|
| EP | 2649983 | * | 10/2013 |
| WO | WO2004096216 A | * | 11/2004 |

OTHER PUBLICATIONS

Encyclopedia of Mental disorders Forum (2006).*
Bellew et al., "Pathogenesis of acne vulgaris: what's new, what's interesting and what may be clinically relevant," J Drugs Dermatol. 10(6): 582-5 (2011).
Fulton, "Acne vulgaris," Emedicine. <emedicine.medscape.com/article/1069804-overview> May 2013.
Heckmann et al., "Botulinum toxin type a injection in the treatment of lichen simplex: an open pilot study," J Am Acad Dermatol. 46(4):617-9 (2002).
Li et al., "Regulation of lipid production by acetylcholine signalling in human sebaceous glands," J Dermatol Sci. 72(2): 116-22 (2013).
Kurokawa et al., "New developments in our understanding of acne pathogenesis and treatment.," Exp Dermatol. 18(10): 821-32 (2009).
Kurzen et al., "Functional characterization of the epidermal cholinergic system in vitro," J Invest Dermatol. 126(11): 2458-72 (2006).
Rose et al., "Safety and efficacy of intradermal injection of botulinum toxin for the treatment of oily skin," Dermatol Surg. 39(3 Pt 1): 443-8 (2013).
Shah, "Use of intradermal botulinum toxin to reduce sebum production and facial pore size," J. Drugs Dermatol. 7(9): 847-50 (2008).
Nebster, "Evidence-based review: fixed-combination therapy and topical retinoids in the treatment of acne," J Drugs Dermatol. 10(6):636-44 (2011).
Zaenglein et al., Acne Vulgaris and Acneiform Eruptions. Fitzpatrick's Dermatology in General Medicine, Seventh Edition. Wolff et al editors, pp. 609-702 (2008).
Zanchi et al., "Botulinum toxin type-A for the treatment of inverse psoriasis," J Eur Acad Dermatol Venereol. 22(4): 431-6 (2008).

* cited by examiner

*Primary Examiner* — Shirley V Gembeh
(74) *Attorney, Agent, or Firm* — McCarter & English, LLP; Danielle L. Herritt, Esq.; Marcie B. Clarke

(57) ABSTRACT

The present invention provides antagonists of acetylcholine receptors for the treatment of skin conditions. The present invention achieves treatment of skin conditions without causing the severe damage to the skin associated with antagonism of nicotinic acetylcholine receptors.

25 Claims, 2 Drawing Sheets

METHODS TO TREAT, PREVENT, AND IMPROVE SKIN CONDITIONS

RELATED APPLICATIONS

Figure 1:
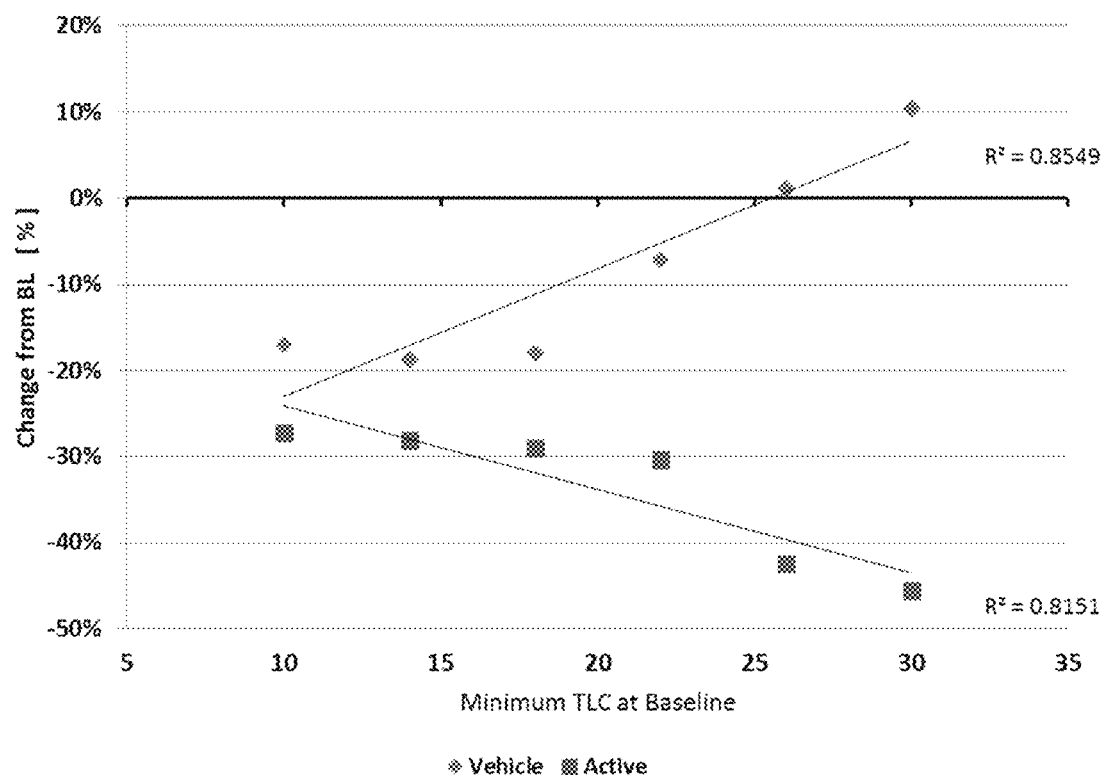

This application claims priority to and benefit of U.S. Provisional application Ser. No. 61/987,103 filed May 1, 2014, the entire contents of which are incorporated herein by reference.

BACKGROUND

It is known in the art that various skin conditions can be treated, improved, and/or prevented by reducing release of endogenous acetylcholine (e.g., through administration of inhibitors of release, such as *botulinum*). For example, see Suskind (2007) for the use of *botulinum* to treatment of acne or Sanders (2007) for the use of *botulinum* to treat excess sebum production, seborrhea, sebaceous hyperplasia, seborrhoeic dermatitis. See also Shah (2008), Li (2013) and Rose (2013) for the use of *botulinum* to treat excess sebum production and enlarged pore size. Other skin conditions that may benefit from treatment with *botulinum* (i.e., from treatment with an inhibitor of acetylcholine release) include, for example, rosacea (See Sanders (2012), psoriasis (Zanchi (2008)) and/or lichen simplex (Heckmann (2002)).

A recent publication confirms that nicotinic receptors may modulate sebum production (See Li (2103)). However, neither this publication nor other current reviews of the field of treating highly prevalent diseases such as acne, where excess sebum production is well known to be a key part of disease pathogenesis (See Zanglein (2008), Kurokawa (2009), Bellew (2011), and Fulton (2013)), specifically teach or suggest use of acetylcholine receptor antagonists. At least one reason that researchers and/or reviewers might not have previously suggested such strategies is due to the above-noted understanding that such agents as nicotinic receptor antagonists cause significant skin damage.

The skin damage known to be caused by nicotinic acetylcholine receptor antagonists, thought to render them unsuitable for use as agents to treat skin conditions, includes, for example, acantholysis. Please see Kurzen (2006). Acantholysis is the separation of individual epidermal keratinocytes from their neighbor, as in conditions such as pemphigus *vulgaris*. It is also described as the loss of intercellular connections, such as desmosomes, resulting in loss of cohesion between keratinocytes, again as seen in diseases such as pemphigus *vulgaris*. Clinical presentations of acantholysis include but are not limited to the appearance of blisters, pruritic eruptions, papules, acneiform lesions, vesicles, pustules, and/or bullous lesions.

SUMMARY

The present disclosure provides particular methods and compositions as described herein.

In certain embodiments, the present disclosure provides methods of treating a skin condition comprising a step of administering to a subject suffering from or susceptible to a skin condition a substance that antagonizes acetylcholine receptors. In some embodiments, the skin condition is selected from the group consisting of acne (in all its forms including acne *vulgaris*), excess sebum production, seborrhea, sebaceous hyperplasia, seborrheic dermatitis, sebaceous adenoma, sebaceous carcinoma, sebaceous cyst, wrinkles, oily skin, or enlarged skin pores. In some embodiments, the step of administering comprises administering the substance according to a regimen that has been established not to cause clinically visible skin lesions due to acantholysis in a majority of treated patients. In some embodiments, the acetylcholine receptors are nicotinic receptors. In some embodiments, the step of administering treats the skin condition. In some embodiments, the step of administering improves the skin condition. In some embodiments, the step of administering improves the appearance of the skin condition. In some embodiments, the step of administering is performed prior to appearance of one or more features of the skin condition on the subject. In some embodiments, the step of administering delays onset of or reduces severity or frequency of the one or more features of the skin condition. In some embodiments, the substance that antagonizes acetylcholine receptors is selected from the group consisting of atracurium besylate, benztropine, biperiden, caramiphen, chlorisondamine, decamethonium bromide, dextromethorphan, dextrorphan, doxacurium, ethopropazine, gantacurium, hexamethonium, mecamylamine, memantine, methyllycaconitine, metocurine iodide, mivacurium chloride, panchronium bromide, pipecuronium, procyclidine, quinolizidine, rocuronium bromide, succinylcholine chloride, temchine, tempoxime hydrochloride, tetracaine, trihexyphenidyl, trimethaphan, tubocurarine, and vecuronium bromide. In some embodiments, the step of administering comprises a route of administration selected from the group consisting of topical, injected, oral and transmucosal administration. In some embodiments, the step of administering comprises administering a composition that is formulated as a topical pharmaceutical composition, injectable pharmaceutical composition, transmucosal pharmaceutical composition, oral pharmaceutical composition, or cosmetic.

In certain embodiments, the present disclosure provides methods of administering a substance that antagonizes acetylcholine receptors to a subject suffering from a condition selected from the group consisting of lichen simplex, psoriasis, rosacea, lupus, scleroderma, Raynaud's syndrome, pruritus, vitiligo, hair loss, wrinkles, and atopic dermatitis. In some embodiments, the step of administering comprises a regimen that has been established not to cause clinically visible skin lesions due to acantholysis in a majority of treated patients. In some embodiments, the acetylcholine receptors are nicotinic receptors. In some embodiments, the step of administering treats the condition. In some embodiments, the step of administering improves the condition. In some embodiments, the step of administering improves the appearance of the condition. In some embodiments, the step of administering is performed prior to appearance of one or more features of the condition in the subject. In some embodiments, the step of administering delays onset of or reduces severity or frequency of the one or more features of the condition. In some embodiments, the substance that antagonizes acetylcholine receptors is selected from the group consisting of atracurium besylate, benztropine, biperiden, caramiphen, chlorisondamine, decamethonium bromide, dextromethorphan, dextrorphan, doxacurium, ethopropazine, gantacurium, hexamethonium, mecamylamine, memantine, methyllycaconitine, metocurine iodide, mivacurium chloride, panchronium bromide, pipecuronium, procyclidine, quinolizidine, rocuronium bromide, succinylcholine chloride, temchine, tempoxime hydrochloride, tetracaine, trihexyphenidyl, trimethaphan, tubocurarine, and vecuronium bromide. In some embodiments, the step of administering comprises a route of administration selected from the group consisting of topical, injected, oral and transmucosal administration. In some embodiments, the step of administering comprises administering a composition that is formulated as a topical pharmaceutical composition, injectable pharmaceutical composition, transmucosal pharmaceutical composition, oral pharmaceutical composition, or cosmetic. In some embodiments, the topical pharmaceutical composition comprises a lotion, cream, gel, liniment, wipe or pad. In some embodiments, the cosmetic comprises a lotion, cream, gel, serum, sunscreen, moisturizer, wipe, pad or foundation.

In certain embodiments, the present disclosure provides topical pharmaceutical compositions comprising an active ingredient comprising atracurium besylate, benztropine, biperiden, caramiphen, chlorisondamine, decamethonium bromide, dextromethorphan, dextrorphan, doxacurium, ethopropazine, hexamethonium, mecamylamine, memantine, methyllycaconitine, metocurine iodide, mivacurium chloride, panchronium bromide, pipecuronium, procyclidine, quinolizidine, rocuronium bromide, succinylcholine chloride, temchine, tempoxime hydrochloride, tetracaine, trihexyphenidyl, trimethaphan, tubocurarine, vecuronium bromide, or combinations thereof, wherein the composition is formulated so that administration of the topical pharmaceutical composition to the skin of a subject has been established not to cause clinically visible skin lesions due to acantholysis in a majority of treated patients. In some embodiments, the composition comprises a percentage by weight of the active ingredient between 20% and 0.0009%. In some embodiments, the percentage by weight of the active ingredient is 10%, 5%, 3%, 2%, 1%, 0.5%, 0.1%, 0.05%, 0.01%, or 0.001%.

BRIEF DESCRIPTION OF THE DRAWING

FIG. 1 shows an exemplary graph that maps the change from baseline in percent reduction of Total Lesion Count for a topical *botulinum* treatment and its control vehicle as a function of Baseline Total Lesion Count for subjects in a study observing the effects of a topical *botulinum* treatment on acne after a single treatment. There is a strong positive correlation between clinical response to treatment with the topical *botulinum* treatment and the baseline severity of disease. There is a strong negative correlation between clinical response to treatment with the control vehicle and the baseline severity of disease.

FIG. 2 shows an exemplary graph that maps the treatment effect (the difference between Active and Vehicle effects on Total Lesion Count) of a topical *botulinum* treatment for acne as a function of Baseline Total Lesion Count for subjects in a study observing the effects of a topical *botulinum* treatment on acne after a single treatment. There is a strong positive correlation between clinical response to treatment and the baseline severity of disease.

DEFINITIONS

Acetylcholine receptor: As used herein, the term "acetylcholine receptor" refers to receptors that respond to acetylcholine. Nicotinic acetylcholine receptors (nAChR, also known as "ionotropic" acetylcholine receptors) are particularly responsive to nicotine. Muscarinic acetylcholine receptors (mAChR, also known as "metabotropic" acetylcholine receptors) are particularly responsive to muscarine. Nicotinic and muscarinic are the two main kinds of "cholinergic" receptors.

Administration: As used herein, the term "administration" refers to the administration of a composition to a subject or system (e.g., to a cell, organ, tissue, organism, or relevant component or set of components thereof). Those of ordinary skill will appreciate that route of administration may vary depending, for example, on the subject or system to which the composition is being administered, the nature of the composition, the purpose of the administration, etc. In some embodiments, administration may involve intermittent dosing. In some embodiments, administration may involve continuous dosing (e.g., perfusion) for at least a selected period of time.

Antagonist: As used herein, the term "antagonist" refers to a receptor antagonist, which is a type of receptor ligand or drug that blocks or dampens agonist-mediated responses rather than provoking a biological response itself upon binding to a receptor. In pharmacology, antagonists have affinity but no efficacy for their cognate receptors, and binding will disrupt the interaction and inhibit the function of an agonist or inverse agonist at receptors. Antagonists mediate their effects by binding to the active (orthosteric) site or to allosteric sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist-receptor binding. The majority of drug antagonists achieve their potency by competing with endogenous ligands or substrates at structurally defined binding sites on receptors.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Biologically active: As used herein, refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

Combination therapy: As used herein, the term "combination therapy" refers to those situations in which a subject is simultaneously exposed to two or more therapeutic regimens or modalities (e.g., to two or more therapeutic agents). In some embodiments, two or more regimens or modalities are administered or applied simultaneously (e.g., one or more individual doses of each of two or more agents, may be administered at substantially the same time); in some embodiments, such regimens or modalities may be administered sequentially (e.g., at least a first dose of a first agent is administered prior to at least a first dose of a second agent); in some embodiments, such regimens or modalities such that individual doses or applications overlap.

Comparable: As used herein, the term "comparable" describes two (or more) sets of conditions, circumstances, individuals, or populations that are sufficiently similar to one another to permit comparison of results obtained or phenomena observed. In some embodiments, comparable sets of conditions, circumstances, individuals, or populations are characterized by a plurality of substantially identical features and one or a small number of varied features. Those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied. Those skilled in the art will appreciate that relative language used herein (e.g., enhanced, activated, reduced, inhibited, etc) will typically refer to comparisons made under comparable conditions.)

Dosage form: (or "unit dosage form"), as used herein, refers to physically discrete unit of a therapeutic agent for a subject (e.g., a human patient) to be treated. In some embodiments, each unit contains a predetermined quantity of active material calculated or demonstrated to produce a desired therapeutic effect when administered to a relevant population according to an appropriate dosing regimen. For example, in some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). It will be understood, however, that the total dosage (e.g., total daily dosage) administered to any particular patient will typically be selected by a medical professional (e.g., a medical doctor) within the scope of sound medical judgment, and may include more than one such discrete unit, and/or may utilize a fraction of a discrete unit.

Dosing regimen: (or "therapeutic regimen"), as used herein is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, a therapeutic agent is administered once a day (QD) or twice a day (BID). In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Improve, increase, reduce, etc: As used herein, terms such as "improve", "increase", "reduce", etc., which necessarily imply a comparison, refer to a comparison with an appropriate comparable reference or standard. For example, in some embodiments, level and/or activity of an agent or marker of interest may be reduced under a set of conditions or circumstances of interest (e.g., after administration of therapy) as compared with its level and/or activity under a comparable set of conditions (e.g., prior to administration of the therapy or after administration of the therapy to an appropriate reference subject). In some embodiments, an appropriate reference may be a historical reference. In some embodiments, an appropriate reference may be an average, e.g., as may be observed within or across a relevant population.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans). In some embodiments, a subject is a human.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition (e.g., wounds, abnormal skin cell proliferation, tissue connective diseases such as scleroderma, pachyonychia congenita, skin inflammation, psoriasis, sunburn or other types of skin damage, skin cancer, etc.) has been diagnosed with or exhibits symptoms of the disease, disorder, or condition.

Symptoms are reduced: According to the present invention, "symptoms are reduced" when one or more symptoms of a particular disease, disorder or condition is reduced in magnitude (e.g., intensity, severity, etc.) or frequency. For purposes of clarity, a delay in the onset of a particular symptom is considered one form of reducing the frequency of that symptom. To give but a few examples, where the condition in question is acne, symptoms of that condition are reduced when the (e.g., diameter, volume, etc.) and/or severity (e.g., redness, inflammatory response, etc.) of one or more blemishes in the selected area is reduced, and/or when the number of total blemishes is reduced (e.g., on a subject's face, back, etc.). Where the condition in question is hyperhidrosis and/or unwanted sweating, symptoms are reduced when the subject produces less sweat. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutically effective amount: As used herein, the term "therapeutically effective amount" means an amount that is sufficient, when administered to a population suffering from or susceptible to a disease, disorder and/or condition, to treat the disease, disorder and/or condition. In some embodiments, a therapeutically effective amount is one that reduces the incidence and/or severity of, and/or delays onset of, one or more symptoms of the disease, disorder and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues. Those of ordinary skill in the art will appreciate that, in some embodiments, a therapeutically effective agent may be formulated and/or administered in a single dose. In some embodiments, a therapeutically effective agent may be formulated and/or administered in a plurality of doses, for example, as part of a dosing regimen.

Therapeutic agent: As used herein, the phrase "therapeutic agent" refers to any agent that, when administered to a subject, has a therapeutic effect and/or elicits a desired biological and/or pharmacological effect.

Treatment: As used herein, the term "treatment" (also "treat" or "treating") refers to any administration of a substance (e.g., provided compositions) that partially or completely alleviates, ameliorates, relives, inhibits, delays onset of, reduces severity of, and/or reduces incidence of one or more symptoms or features of a particular disease, disorder and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder and/or condition.

Unwanted side effects: As used herein, the term "unwanted side effects" refers to one or more effects and/or symptoms associated with administration of a substance to a patient that are not the desired and/or intended effects and/or are unpleasant to the patient. Exemplary unwanted side effects include pain; bruising; ecchymosis; hematoma; *botulism* poisoning; unwanted systemic effects; undesirable blood levels of the administered substance; damage to underlying nervous tissue (e.g., neuronal paralysis); unwanted effects on muscles (e.g., muscle paralysis); flu-like symptoms; morbidity; mortality; alteration in body weight; alteration in enzyme levels; pathological changes detected at the microscopic, macroscopic, and/or physiological levels; infection; hemorrhage; inflammation; scarring; loss of function; changes in local blood flow; fever; malaise; teratogenesis; pulmonary hypertension; stroke; heart disease; heart attack; neuropathy; nausea; vomiting; dizziness; diarrhea; headache; dermatitis; dry mouth; addiction; miscarriage; abortion; uterine hemorrhage; birth defects; bleeding; cardiovascular disease; deafness; kidney damage and/or failure; liver damage and/or failure; dementia; depression; diabetes; erectile dysfunction; glaucoma; hair loss; anemia; insomnia; lactic acidosis; melasma; thrombosis; priapism; rhabdomyolysis; seizures; drowsiness; increase in appetite; decrease in appetite; increase in libido; decrease in libido; tardive dyskinesia; non-axillary sweating; injection site pain and hemorrhage; pharyngitis; neck pain; back pain; pruritus; anxiety; follicular obstruction; and/or combinations thereof. In some embodiments, topical administration of a provided composition reduces unwanted side effects by about 50%, about 60%, about 70%, about 80%, about 90%, about 95%, about 98%, about 99%, or about 100% relative to non-topical administration (e.g., injection, oral administration, etc.) of the same substance.

DESCRIPTION OF CERTAIN EMBODIMENTS

The present invention teaches the use of antagonists of acetylcholine receptors (e.g., muscarinic receptors and/or nicotinic receptors) for the treatment of certain skin conditions. In particular, the present invention relates to treatment of skin conditions that benefit from modulation of acetylcholine.

As noted above, it is known in the art that various skin conditions can be treated, improved, and/or prevented by reducing release of endogenous acetylcholine (e.g., through administration of inhibitors of release, such as *botulinum*). For example, see Suskind (2007) for the use of *botulinum* to treatment of acne or Sanders (2007) for the use of *botulinum* to treat excess sebum production, seborrhea, sebaceous hyperplasia, seborrhoeic dermatitis. See also Shah (2008), Li (2013) and Rose (2013) for the use of *botulinum* to treat excess sebum production and enlarged pore size. Any or all of these conditions may be treated, improved, and/or prevented in accordance with the present invention.

Other skin conditions that may benefit from treatment with *botulinum* (i.e., from treatment with an inhibitor of acetylcholine release) include, for example, rosacea (See Sanders (2012), psoriasis (Zanchi (2008)) and/or lichen simplex (Heckmann (2002)). Any or all of these conditions may be treated, improved, and/or prevented in accordance with the present invention.

Acetylcholine Receptor Antagonists

The present invention appreciates that, because it has been established that agents (e.g., *botulinum*) that act to prevent the release of acetylcholine from nerve and other cells can treat these conditions, and it is likely that such methods effectively reduce stimulation of skin cells, such as sebocytes, that respond pathologically to such stimulation to cause these unwanted skin conditions, an alternative strategy for treating such disorders would be to use an acetylcholine receptor antagonist.

There are two types of cell receptors for acetylcholine: muscarinic and nicotinic. The present invention encompasses administration of antagonists of either type of acetylcholine receptor. In some embodiments, antagonists of nicotinic receptors are employed. In some embodiments, antagonists of muscarinic receptors are employed. Appropriate acetylcholine receptor antagonists for use in accordance with the present invention will be apparent to those skilled in the art, reading the present disclosure, and include, for example, any of atracurium besylate, benztropine, biperiden, caramiphen, chlorisondamine, decamethonium bromide, dextromethorphan, dextrorphan, doxacurium, ethopropazine, gantacurium, hexamethonium, mecamylamine, memantine, methyllycaconitine, metocurine iodide, mivacurium chloride, panchronium bromide, pipecuronium, procyclidine, quinolizidine, rocuronium bromide, succinylcholine chloride, temchine, tempoxime hydrochloride, tetracaine, trihexyphenidyl, trimethaphan, tubocurarine, and vecuronium bromide.

Nicotinic

A recent publication confirms that nicotinic receptors may modulate sebum production. See Li (2103). However, neither this publication nor other current reviews of the field of treating highly prevalent diseases such as acne, where excess sebum production is well known to be a key part of disease pathogenesis (See Zanglein (2008), Kurokawa (2009), Bellew (2011), and Fulton (2013)), specifically teach or suggest use of acetylcholine receptor antagonists. Without wishing to be bound by any particular theory, we propose that at least one reason that researchers and/or reviewers might not have previously suggested such strategies is due to the above-noted understanding that such agents as nicotinic receptor antagonists cause significant skin damage. The present disclosure provides the surprising teaching that an antagonist of the nicotinic acetylcholine receptor can be used to treat skin conditions without such significant skin damage.

The skin damage known to be caused by nicotinic acetylcholine receptor antagonists, previously thought to render them unsuitable for use as agents to treat skin conditions, includes, for example, acantholysis. See Kurzen (2006). Acantholysis is the separation of individual epidermal keratinocytes from their neighbor, as in conditions such as pemphigus *vulgaris*. It is also described as the loss of intercellular connections. such as desmosomes, resulting in loss of cohesion between keratinocytes, again as seen in diseases such as pemphigus *vulgaris*. Clinical presentations of acantholysis include but are not limited to the appearance of blisters, pruritic eruptions, papules, acneiform lesions, vesicles, pustules, and/or bullous lesions. As well, it has been well established that certain devastating skin diseases, such as pemphigus *vulgaris*, are mediated by the destruction of nicotinic acetylcholine receptors by autoantibodies. See Kurzen (2006). Thus, prior to the present disclosure, it was well established that antagonizing or destroying these receptors is expected to result in extreme skin damage and pathology, and that agents that antagonize or destroy such receptors are expected to be unsuitable for use an agent treat skin conditions. The present invention discloses that use of such agents to treat skin conditions can be achieved without significant skin damage and/or signs of acantholysis and/or cell death.

The present invention encompasses the recognition that nicotinic acetylcholine receptor pharmacologic antagonists can surprisingly be used safely to treat skin because it was determined that there can be a level nicotinic acetylcholine receptor antagonists that will treat, improve and/or prevent unwanted skin conditions without causing skin damage such as due to acantholysis (e.g., without causing one or more of the clinical presentations associated with acantholysis). The present invention is based on newly discovered and surprising understandings of how highly dis-regulated or diseased skin cells respond differently to pharmacologic agents impacting acetylcholine-mediated skin conditions than healthy or mildly dis-regulated or diseased skin cells.

Therapeutic Dosage

Current belief in the field of dermatology is that patients with skin conditions such as acne respond to a given treatment at a given dose proportionately to the severity of their illness. For example, if hypothetical Patient A has 100 acne lesions on her face and hypothetical Patient B has 50 lesions on her face and they each receive a 50 mg pill of Agent X that has been shown to be an effective treatment for acne, then if Patient A has 50% reduction in the number of acne lesions (which in her case would be a reduction by 50 lesions) it would be expected that Patient B would have approximately a 50% reduction in acne lesions (which in her case would a reduction by 25 lesions). This assumption enables the comparison of patients within a study despite different patients being enrolled in the study with different levels of baseline disease severity. This assumption essentially "normalizes" changes in disease state due to treatment by reference to each patient's own baseline of disease. This assumption not only enables the comparison of patients within a study despite different patients being enrolled in the study with different levels of baseline disease severity, but it also enables the comparison of results across studies of similar (e.g., one retinoid cream versus another) or different treatments (e.g., a retinoid cream versus an antibiotic cream) for acne. The different treatments can be compared across studies by comparing the percent reductions in acne lesions for each treatment/study. See Webster (2011) who summarizes dozens of standard acne treatment clinical studies that use percent reductions in acne lesions as study outcome measures; Webster then compares these study results against one another using this same percent reduction in acne lesions for differing treatments.

Figure 2:
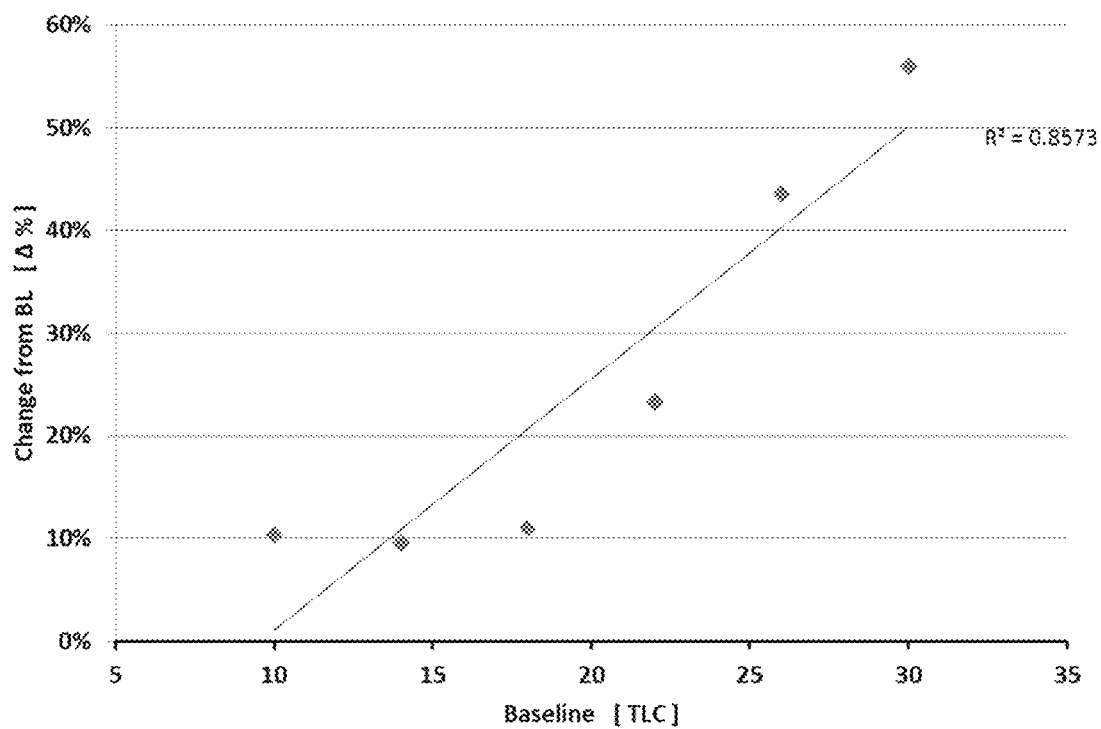

An analysis of clinical study data by the inventor finds that the fundamental assumption made about the proportionality of pharmacologic response is incorrect. The clinical trial generating this data studied the effect of a topical *botulinum* treatment on acne. Acne lesion counts were made by the investigator at baseline prior to treatment and then after treatment. Please see FIGS. 1-4, which demonstrate that the greater the baseline disease severity that a patient had, the disproportionately greater response to treatment that a patient had, although all patients received the same dose of drug. In fact, the percent reduction in lesion count was highly correlated to baseline disease severity as noted in the FIGS. 1-2 week over week that the patients were observed. Thus, in the example above, Patient A might actually be observed to have 75% reduction in acne lesions, while Patient B might actually be observed to have 50% reduction in acne lesions. The implications of these unexpected and surprising findings are that patients having more diseased states (e.g., severe) would respond to a much greater extent than subjects who have less diseased states (e.g., mild). Since disease covers a spectrum, the far end of one spectrum is no disease, going to mild, then moderate, and finally severe disease. Thus, a drug dose that is toxic to skin at a high dose by mechanism "X" (e.g., acantholysis) may have no effect on skin at a low dose. In turn, because the severely diseased skin (e.g., acne) caused by mechanism "Y" (hyper-sebum production) is so dysregulated it is hypersensitive to this low dose and is, in fact, therapeutic. While therapeutic in treating the acne, the drug does not cause acantholysis in the rest of the skin.

Thus, unexpectedly and surprisingly, it was found that there could be a dose of an antinicotinic acetylcholine antagonist that could effectively treat a skin condition without causing clinically observable lesions caused by acantholysis and skin cell death.

The invention provides the use of substances that antagonize acetylcholine receptors at a level that will effectively treat, improve or prevent skin conditions without otherwise causing clinically visible lesions due to acantholysis. Such substances may primarily be an antagonist of nicotinic acetylcholine receptors or may primarily affect a different receptor but secondarily be an antagonist of acetylcholine receptors due to cross-reactivity of the substance to such receptors. Skin conditions may include, but are not limited to, such skin conditions as acne (in all its forms including acne *vulgaris*), excess sebum production, seborrhea, sebaceous hyperplasia, seborrhoeic dermatitis, sebaceous adenoma, sebaceous carcinoma, sebaceous cyst, oily skin, enlarged skin pores, lichen simplex, psoriasis, rosacea, lupus, scleroderma, Raynaud's syndrome, pruritus, vitiligo, hair loss, wrinkles, or atopic dermatitis.

Appropriate acetylcholine receptor antagonists for use in accordance with the present invention will be apparent to those skilled in the art, reading the present disclosure, and include, for example, any of atracurium besylate, benztropine, biperiden, caramiphen, chlorisondamine, decamethonium bromide, dextromethorphan, dextrorphan, doxacurium, ethopropazine, hexamethonium, mecamylamine, memantine, methylcaconitine, metocurine iodide, mivacurium chloride, panchronium bromide, pipecuronium, procyclidine, quinolizidine, rocuronium bromide, succinylcholine chloride, temchine, tempoxime hydrochloride, tetracaine, trihexyphenidyl, trimethaphan, tubocurarine, or vecuronium bromide, or combinations thereof.

Appropriate formulations (e.g., topical formulations) of acetylcholine receptor antagonists for use in accordance with the present invention will be apparent to those skilled in the art reading the present disclosure. In many embodiments, useful topical formulations are between 10% and 0.0009% by weight the active ingredient or specifically 10%, 5%, 3%, 2%, 1%, 0.5%, 0.1%, 0.05%, 0.01%, or 0.001% by weight.

Diseases, Disorders and/or Conditions

The present invention provides methods and compositions for the treatment and/or prevention of any of a variety of diseases, disorders and/or conditions. In some embodiments, the present invention provides methods and compositions for the treatment and/or prevention of lichen simplex, psoriasis, rosacea, lupus, scleroderma, Raynaud's syndrome, pruritus, vitiligo, hair loss, wrinkles, and atopic dermatitis.

In some embodiments, the present invention involves administration of at least one provided composition according to a dosing regimen sufficient to achieve a reduction in the degree and/or prevalence of a relevant condition of at least about 20%; in some embodiments according to a dosing regimen sufficient to achieve a of at least about 25%; in some embodiments according to a dosing regimen sufficient to achieve a reduction of at least about 30%; in some embodiments according to a dosing regimen sufficient to achieve a reduction of at least about 31%, about 32%, about 33%, about 34%, about 35%, about 36%, about 37%, about 38%, about 39%, about 40%, about 41%, about 42%, about 43%, about 44%, about 45, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, or more.

In some embodiments, the present invention involves administration of at least one provided composition according to a dosing regimen sufficient to achieve a reduction in the degree and/or prevalence of a relevant condition of at least about 20% in a specified percentage of a population of patients to which the composition was administered; in some embodiments according to a dosing regimen sufficient to achieve a of at least about 25% in a specified percentage of a population of patients to which the composition was administered; in some embodiments according to a dosing regimen sufficient to achieve a reduction of at least about 30% in a specified percentage of a population of patients to which the composition was administered; in some embodiments according to a dosing regimen sufficient to achieve a reduction of at least about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90% or more in a specified percentage of a population of patients to which the composition was administered. In some embodiments, the specified percentage of population of patients to which the composition was administered is at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. To give but a few illustrative examples, in some embodiments, the present invention involves administration of at least one provided composition according to a dosing regimen sufficient to achieve a reduction in the degree and/or prevalence of a relevant dermatologic condition of at least about 20% in at least about 50% of the population of patients to which the composition was administered. In some embodiments, the present invention involves administration of at least one provided composition according to a dosing regimen sufficient to achieve a reduction in the degree and/or prevalence of a relevant dermatologic condition of at least about 30% in at least about 50% of the population of patients to which the composition was administered.

The present invention provides methods of treating and/or preventing a dermatologic condition comprising administration of a provided composition to a subject suffering from, susceptible to, and/or displaying symptoms the condition. In some embodiments, provided compositions for treatment of a condition as described herein are formulated for any route of administration described herein. In some embodiments, provided compositions are formulated for topical administration. In some embodiments, provided compositions are formulated into a cream, liniment, lotion, gel, shampoo, conditioner, sunscreen, deodorant, and/or antiperspirant (e.g., as a roll-on, solid stick, gel, cream, aerosol, etc.), etc., as appropriate to the condition being treated.

In some embodiments, provided compositions are formulated for injection, e.g., into an affected site. In some embodiments, provided compositions are formulated for systemic delivery.

In some embodiments, such a provided composition is administered locally to an affected site (e.g., axillae, hands, feet, scalp, hair follicle, face, neck, back, arms, chest, etc., as appropriate to the particular condition being treated). In some embodiments, local administration is achieved by topical administration and/or by injection. In some embodiments, a provided composition is administered systemically (e.g., orally, topically, via injection, etc.).

Further considerations for formulation and administration are described in further detail in the sections entitled "Compositions and Formulations" and "Administration."

More detailed discussion of certain of these conditions and their treatment and/or prevention in accordance with the present invention is provided below.

Skin Diseases, Disorders and/or Conditions

The present invention provides methods and compositions for the treatment and/or prevention of any of a variety of skin diseases, disorders and/or conditions. In some embodiments, the present invention provides methods and compositions for the treatment and/or prevention of diseases, disorders, or conditions associated with activity of sweat and/or sebaceous glands. In some embodiments, the present invention provides methods and compositions for the treatment and/or prevention of diseases, disorders or conditions associated with the epidermal and/or dermal level of the skin.

In some embodiments, the present invention provides methods and compositions for the treatment and/or prevention of one or more of acne (in all its forms including acne *vulgaris*), excess sebum production, seborrhea, sebaceous hyperplasia, seborrheic dermatitis, sebaceous adenoma, sebaceous carcinoma, sebaceous cyst, oily skin, enlarged skin pores, and/or combinations thereof.

Compositions and Formulations

As described herein, provided compositions are useful in various cosmetic and/or medical applications. Such compositions may be administered to a subject by any available route, including, but not limited to, oral (PO), intravenous (IV), intramuscular (IM), intraarterial, intramedullary, intrathecal, subcutaneous (SQ), intraventricular, transdermal, interdermal, intradermal, rectal (PR), vaginal, intraperitoneal (IP), intragastric (IG), topical and/or transdermal (e.g., by lotions, creams, powders, ointments, liniments, gels, drops, wipes, pads, etc.), mucosal; and/or combinations of any of the foregoing.

Formulations of provided compositions may be prepared by any appropriate method, for example as known or hereafter developed in the art of pharmacology. In general, such preparatory methods include the step of bringing a provided composition into association with one or more excipients, and then, if necessary and/or desirable, shaping and/or packaging the product into an appropriate form for administration, for example as or in a single- or multi-dose unit.

In some embodiments, compositions may be prepared, packaged, and/or sold in bulk, as a single unit dose, and/or as a plurality of single unit doses. As used herein, a "unit dose" is a discrete amount of the pharmaceutical composition comprising a predetermined amount of the provided composition. The amount of the provided composition is generally equal to the dosage of the provided composition which would be administered to a subject and/or a convenient fraction of such a dosage such as, for example, one-half or one-third of such a dosage.

Appropriate excipients for use in compositions (e.g., pharmaceutically and/or cosmetically acceptable compositions) may, for example, include one or more excipients such as solvents, dispersion media, granulating media, diluents, or other liquid vehicles, dispersion or suspension aids, surface active agents and/or emulsifiers, isotonic agents, thickening or emulsifying agents, preservatives, solid binders, lubricants, disintegrating agents, binding agents, preservatives, buffering agents and the like, as suited to the particular dosage form desired. Alternatively or additionally, excipients such as cocoa butter and/or suppository waxes, coloring agents, coating agents, sweetening, flavoring, and/or perfuming agents can be utilized. Remington's The Science and Practice of Pharmacy, 21st Edition, A. R. Gennaro (Lippincott, Williams & Wilkins, Baltimore, Md., 2005; incorporated herein by reference) discloses various excipients used in formulating pharmaceutical compositions and known techniques for the preparation thereof.

In some embodiments, an appropriate excipient (e.g., a pharmaceutically and/or cosmetically acceptable excipient) is at least 95%, at least 96%, at least 97%, at least 98%, at least 99%, or 100% pure. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or other International Pharmacopoeia.

In some embodiments, provided compositions are formulated as a cream, liniment, ointment, oil, foam, spray, lotion, liquid, powder, thickening lotion, gel, wipe or pad (e.g., formulated for dermal/transdermal delivery as described herein). Particular exemplary such formulations may be prepared, for example, as cosmetic formulation products such as skin softeners, nutritional lotion type emulsions, cleansing lotions, cleansing creams, skin milks, emollient lotions, massage creams, emollient creams, make-up bases, foundations, lipsticks, facial packs or facial gels, sunscreens, gels, moisturizers, wipes, pads, cleaner formulations such as shampoos, rinses, body cleansers, hair-tonics, or soaps, or dermatological compositions such as lotions, creams, gels, serums, sunscreens, moisturizers, wipes, pads, ointments, liniments, patches, deodorants, or sprays.

In some embodiments, provided compositions (e.g., provided compositions formulated for topical, and particularly for dermal/transdermal administration) are formulated with cosmetically acceptable components. For example, in some embodiments, provided compositions are formulated with water and also any cosmetically acceptable solvent, in particular, monoalcohols, such as alkanols having 1 to 8 carbon atoms (like ethanol, isopropanol, benzyl alcohol and phenylethyl alcohol), polyalcohols, such as alkylene glycols (like glycerine, ethylene glycol and propylene glycol), and glycol ethers, such as mono-, di-, and tri-ethylene glycol monoalkyl ethers, for example, ethylene glycol monomethyl ether and diethylene glycol monomethyl ether, used singly or in a mixture. Such components can be present, for example, in proportions of up to as much as 60%, 70%, 80%, or 90% by weight, relative to the weight of the total composition.

In some embodiments, provided compositions for topical administration include one or more cosmetically acceptable components that impart appearance attributes desirable or appropriate to the subject to which the composition is to be applied (e.g., a matte appearance, which may be particularly desirable or appropriate for administration to subjects having greasy skin)

In some embodiments, provided compositions are formulated with at least one cosmetically acceptable filler material, for example, in order to obtain a matte product, which may be especially desired for individuals with greasy skin.

Those of ordinary skill in the art will appreciate that provided compositions may be incorporated into a device such as, for example, a patch. A variety of transdermal patch structures are known in the art; those of ordinary skill will appreciate that provided compositions may readily be incorporated into any of a variety of such structures. In some embodiments, a transdermal patch may further comprise a plurality of needles extending from one side of the patch that is applied to the skin, wherein needles extend from the patch to project through the stratum corneum of the skin. In some embodiments, needles do not rupture a blood vessel.

In some embodiments, a transdermal patch includes an adhesive. Some examples of adhesive patches are well known (for example, see U.S. Design Pat. 296,006; and U.S. Pat. Nos. 6,010,715; 5,591,767; 5,008,110; 5,683,712; 5,948,433; and 5,965,154; all of which are incorporated herein by reference). Adhesive patches are generally characterized as having an adhesive layer, which will be applied to a patient's skin, a depot or reservoir for holding a provided composition, and an exterior surface that prevents leakage of the provided composition from the depot. The exterior surface of a patch is typically non-adhesive.

Liquid dosage forms for oral and/or parenteral administration include, but are not limited to, emulsions, microemulsions, solutions, suspensions, syrups, and/or elixirs. In addition to provided compositions, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such a CREMOPHOR®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of a provided composition, it may be desirable to slow the absorption of the provided composition from subcutaneous or intramuscular injection. This may be accomplished by the use of a liquid suspension of crystalline or amorphous material with poor water solubility. The rate of absorption of the provided composition then depends upon its rate of dissolution which, in turn, may depend upon crystal size and crystalline form. Alternatively, delayed absorption of a parenterally administered provided composition form is accomplished by dissolving or suspending the provided composition in an oil vehicle. Injectable depot forms are made by forming microencapsule matrices of the provided composition in biodegradable polymers such as polylactide-polyglycolide. Depending upon the ratio of provided composition to polymer and the nature of the particular polymer employed, the rate of provided composition release can be controlled. Examples of other biodegradable polymers include poly(orthoesters) and poly(anhydrides). Depot injectable formulations are prepared by entrapping the provided composition in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the provided composition.

Solid dosage forms for oral administration include capsules, tablets, pills, powders, and granules. In such solid dosage forms, the provided composition is mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato starch, tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and/or hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the provided composition(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Administration

As described herein, the present invention provides methods of administering provided compositions to a subject for various applications including, for example, cosmetic and/or medical applications. In some embodiments, the present invention provides methods of treating and/or preventing diseases, disorders, and/or conditions associated with activity of epidermal and/or dermal structures (e.g., sweat glands, sebaceous glands, hair follicles, etc.) by administering provided compositions to a subject in need thereof.

In some embodiments, the present invention provides methods of administration of provided compositions via any route of delivery, including, but not limited to, oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical and/or transdermal (e.g., by lotions, creams, liniments, ointments, powders, gels, drops, wipes, pads, etc.), mucosal; and/or combinations thereof.

In some embodiments, provided methods involve topical, transdermal, or intradermal administration of provided compositions to the skin of a subject. In some embodiments, such routes achieve local delivery.

Therapeutic Agents

In some embodiments, provided compositions comprise one or more therapeutic agents. Therapeutic agents that can be utilized in accordance with the compositions described herein, include, but are not limited to, substances that antagonize acetylcholine receptors. In some embodiments, the substances that antagonize acetylcholine receptors are selected from the group consisting of atracurium besylate, benztropine, biperiden, caramiphen, chlorisondamine, decamethonium bromide, dextromethorphan, dextrorphan, doxacurium, ethopropazine, gantacurium, hexamethonium, mecamylamine, memantine, methyllycaconitine, metocurine iodide, mivacurium chloride, panchronium bromide, pipecuronium, procyclidine, quinolizidine, rocuronium bromide, succinylcholine chloride, temchine, tempoxime hydrochloride, tetracaine, trihexyphenidyl, trimethaphan, tubocurarine, and vecuronium bromide, and/or combinations thereof. In some embodiments, therapeutic agents include any of those described in the section entitled In some embodiments, the therapeutic agent is an active ingredient in a pharmaceutical composition. In some embodiments, the percentage by weight of the active ingredient is between 20% and 0.0009%. In some embodiments, the percentage by weight of the active ingredient is about 10%, 5%, about 3%, about 2%, about 1%, about 0.5%, about 0.1%, about 0.05%, about 0.01%, or about 0.001%.

Combination Therapy

According to the present invention, provided compositions may be administered in combination with one or more other active agents and/or therapeutic modalities, such as known therapeutic agents and/or independently active biologically active agents. In some embodiments, provided compositions include one or more such other active agents; in some embodiments, such other active agents are provided as part of distinct compositions. In some embodiments, combination therapy involves simultaneous administration of one or more doses or units of two or more different active agents and/or therapeutic modalities; in some embodiments, combination therapy involves simultaneous exposure to two or more different active agents and/or therapeutic modalities, for example through overlapping dosing regimens.

In some embodiments, provided compositions include or are administered in combination with one or more other active agents useful for the treatment of the relevant dermatologic or other disease, disorder and/or condition, for example as discussed herein in context of the relevant disease, disorder, and/or condition.

REFERENCES

Suskind et al. 2007, *Botulinum* in the prevention or treatment of acne, U.S. Pat. No. 7,226,605.
Sanders et al. 2007, Treatment of holocrine dysfunction with *clostridia botulinum*, U.S. Pat. No. 7,288,259.
Shah, A R. Use of intradermal *botulinum* to reduce sebum production and facial pore size. J Drugs Dermatol 2008; 7:847-850.

Li et al. Regulation of lipid production by acetylcholine signaling in human sebaceous glands. J Derm Sci 2013; 72:116-122.

Rose et al. Safety and efficacy of intradermal injection of *botulinum* toxin for the treatment of oily skin. Derm Surg 2013; 39:443-448.

Sander et al. 2012, Treatment of rosacea with *clostridium botulinum,* U.S. Pat. No. 8,153,139.

Zanchi et al. *Botulinum* toxin type-A for the treatment of inverse psoriasis. J Eur Acad Dermatol Venereol; 2008 April:22(4):431-6.

Heckmann et al. *Botulinum* toxin type A injection in the treatment of lichen simplex: an open label study. J Am Acad Dermatol; 2002 46(4): 617-9.

Zaenglein et al. "Acne *Vulgaris* and Acneiform Eruptions" in Fitzpatrick's Dermatology in General Medicine, Seventh Edition, Wolff et al editors; 2008, pp. 690-702.

Kurokawa et al. New developments in our understanding of acne pathogenesis and treatment. Exp Dermatol; 2009 18:821-830.

Fulton Acne *vulgaris* 2013 Emedicine, May 2013, can be found on the world wide web at emedicine.medscape-.com/article/1069804-overview Kurzen et al. Functional characterization of the epidermal cholinergic system. J Invest Dermatol; 2006, 126:2458-2472.

Webster G F. Evidenced-based review: fixed-combination therapy and topical retinoids in the treatment of acne. J Drugs Dermatol; 2011 10(6):636-644.

Gennaro A R. Remington's The Science and Practice of Pharmacy, 21st Edition. 2005

Asche H. 1988, Multicompartmentalized transdermal patch for administering drugs to the skin, US Design Pat. 296,006

Wick, J J, et al. 2000, Transdermal patch incorporating a polymer film incorporated with an active agent, U.S. Pat. No. 6,010,715.

Mohr, J M, et al. 1997, Liquid reservoir transdermal patch for the administration of ketorolac, U.S. Pat. No. 5,591,767.

Benecke, A G, et al. 1991, Storage-stable transdermal patch, U.S. Pat. No. 5,008,110.

Cavazza, P. 1997, Transdermal patch for the administration of homeopathic drugs, U.S. Pat. No. 5,683,712.

Burton, S A, et al. 1999, Transdermal patch, U.S. Pat. No. 5,948,433.

Haralambopoulos C. 1999, Adhesive matrix type transdermal patch and method of manufacturing same, U.S. Pat. No. 5,965,154.

EXEMPLIFICATION

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain information, exemplification and guidance, which can be adapted to the practice of this invention in its various embodiments and the equivalents thereof.

Example 1

Clinical Study to Determine the Effect of Dermal Memantine Treatment on Sebum Production and the Health of the Skin A memantine lotion formulation comprising 2% memantine by weight was made. The remaining components in the formulation were inactive, compendial excipients. An identical lotion formulation was made without memantine, which was used as a control treatment. Two 2 cm by 4 cm regions of the back between the scapula and spine were selected for treatment in a 55 year old man. One region was selected for treatment with the memantine formulation and the other region was selected for treatment with the control formulation. Both regions of the skin were healthy skin. Each region was tested for sebum production using Sebotape. The Sebotape was applied to each treatment region for a 60 minute period to assess sebum production. Sebum production for the two regions of the back were observed to be the same prior to any treatment. Each treatment region of the back was treated twice daily with a drop of the memantine or control formulation for a period of 6 days.

After five days, the memantine treatment region demonstrated a marked (>50%) reduction in sebum production (as assessed by the Sebotape) when compared to the skin assessed prior to treatment or when compared to the control region of the skin. After five days, the memantine treatment region was observed to be healthy skin.

After six days, the memantine treatment region again demonstrated a marked (>50%) reduction is sebum production (as assessed by the Sebotape) when compared to the skin assessed prior to treatment or when compared to the control region of the skin. After six days, the memantine treatment region was again observed to be healthy skin. This study demonstrated that memantine may be used to reduce sebum production while maintaining the health of the skin.

Example 2

Treatment of Oily Skin with Acetylcholine Receptor Antagonist

A 37 year old woman who has oily skin starts using a cotton pad to apply a 1% solution of biperiden to her face twice a day. After a month, her skin is expected to appear much less oily and she had no other visible unwanted side-effects regarding her skin.

Example 3

Treatment of Enlarged Skin Pores with Acetylcholine Receptor Antagonist

A 38 year old woman observes that her skin pores appear larger than she would like. She then starts using a cotton pad to apply a 0.1% gel of mecamylamine to her face twice a day. After a month, her skin pores are expected to appear to be smaller in diameter and she had no other visible unwanted side-effects regarding her skin.

Example 4

Treatment of Acne with Acetylcholine Receptor Antagonist

A 18 year old woman observes that she has many acne lesions over her entire face. She then starts using a cotton pad to apply a 0.5% cream of memantine to her face twice a day. After a three months, she is expected to observe that the appearance of face looks better because her acne appears to be less visible than before she started applying the memantine cream and she had no other visible unwanted side-effects regarding her skin.

Example 5

Clinical Study to Evaluate Effect of Acetylcholine Receptor Antagonist on Acne A clinical trial is conducted to assess the therapeutic effects of applying a 3% lotion of trimethan on acne patients. On trial enrollment, these patients are not getting any treatments for acne. Forty patients with moderate to severe acne are enrolled in the clinical trial. Prior to treatment, the acne is assessed by a four-point Investigator Global Assessment Score (None, Mild, Moderate, Severe) and by counting the number of acne lesions on the patients face ("Total Lesion Counts"). Twenty patients are randomly assigned to get twice daily treatments with a topical solution of trimethan and the other twenty patients are assigned to getting a treatment with a topical solution that is the same as the trimethan solution except that it contains no trimethan ("Vehicle Solution"). Neither the physician nor patient know which treatment the patient is getting. After three months, it is expected that 60% of patients who have received the trimethan solution are scored Mild or None on the Investigator Global Assessment score vs. 30% of patients who received the Vehicle Solution. After three months, it is expected that patients who have received the trimethan solution are observed on average to have a 50% reduction in Total Lesion Counts vs. a 30% reduction for patients who have received the Vehicle Solution. Only 3% of subjects treated with trimethan have unwanted side-effects and none of them are severe.

Example 6

Methods to Treat, Prevent, and Improve Skin Conditions

The present invention provides the unexpected and surprising teaching that antagonists of acetylcholine receptor activity (e.g., of nicotinic and/or muscarinic receptors), and particularly of nicotinic acetylcholine receptors, can effectively be developed for the treatment of certain skin conditions.

Prior work has proposed that certain skin conditions might be treated, improved, or prevented by reducing levels of acetylcholine in the skin, for example by reducing the endogenous release of acetylcholine through use of inhibitors of acetylcholine release, such as *botulinum* toxin. Such methods effectively reduce stimulation of skin cells, such as sebocytes, that may respond pathologically to such stimulation to cause unwanted skin conditions, for example, acne (in all its forms including acne *vulgaris*), excess sebum production, seborrhea, sebaceous hyperplasia, seborrhoeic dermatitis, sebaceous adenoma, sebaceous carcinoma, sebaceous cyst, oily skin, enlarged skin pores, psoriasis, rosacea, or atopic dermatitis.

The present invention teaches that pathologic stimulation of skin cells by acetylcholine can be achieved through use of an acetylcholine receptor pharmacologic antagonist, especially an antagonist of the nicotinic acetylcholine receptor. It has been well established that antagonists of nicotinic acetylcholine receptors cause severe damage to the skin (e.g., skin lesions due to acantholysis), creating an expectation in the art that such agents are unsuitable for use as an agent to treat skin conditions. As well, it has been well established that certain devastating skin diseases, such as pemphigus *vulgaris,* are mediated by the destruction of nicotinic acetylcholine receptors by autoantibodies. Thus, prior to the present disclosure, the understanding in the art has been that antagonizing or destroying these receptors will result in extreme skin damage and pathology, such as would be due to acantholysis, making pharmacologic agents that antagonize or destroy such receptors unsuitable for use as an agent to treat skin conditions.

The present invention provides, among other things, a teaching that nicotinic acetylcholine receptor pharmacologic antagonists can in fact be used safely to treat skin because it was surprisingly found that there can be a level nicotinic acetylcholine receptor antagonists that will treat, improve and prevent unwanted skin conditions without causing skin damage. The present invention is based on newly discovered and surprising understandings of how highly dis-regulated or diseased skin cells respond differently to pharmacologic agents impacting acetylcholine-mediated skin conditions when compared to healthy or mildly dis-regulated or diseased skin cells. The invention provides use of substances that antagonize nicotinic acetylcholine receptors at a level that will effectively treat, improve or prevent skin conditions without causing skin lesions due to acantholysis. Such substances may primarily be an antagonist of nicotinic acetylcholine receptors or may primarily affect a different receptor but secondarily be an antagonist of nicotinic acetylcholine receptors due to cross-reactivity of the substance to such receptors.

The present invention teaches the use of antagonists of acetylcholine receptors (e.g., muscarinic receptors and/or nicotinic receptors) for the treatment of certain skin conditions. In particular, the present invention relates to treatment of skin conditions that benefit from modulation of acetylcholine.

As noted above, it is known in the art that various skin conditions can be treated, improved, and/or prevented by reducing release of endogenous acetylcholine (e.g., through administration of inhibitors of release, such as *botulinum*). For example, see Suskind (2007) for the use of *botulinum* to treatment of acne or Sanders (2007) for the use of *botulinum* to treat excess sebum production, seborrhea, sebaceous hyperplasia, seborrhoeic dermatitis. See also Shah (2008), Li (2013) and Rose (2013) for the use of *botulinum* to treat excess sebum production and enlarged pore size. Any or all of these conditions may be treated, improved, and/or prevented in accordance with the present invention.

Other skin conditions that may benefit from treatment with *botulinum* (i.e., from treatment with an inhibitor of acetylcholine release) include, for example, rosacea (See Sanders (2012), psoriasis (Zanchi (2008)) and/or lichen simplex (Heckmann (2002)). Any or all of these conditions may be treated, improved, and/or prevented in accordance with the present invention The present invention appreciates that, because it has been established that agents (e.g., *botulinum*) that act to prevent the release of acetylcholine from nerve and other cells can treat these conditions, and it is likely that such methods effectively reduce stimulation of skin cells, such as sebocytes, that respond pathologically to such stimulation to cause these unwanted skin conditions, an alternative strategy for treating such disorders would be to use an acetylcholine receptor antagonist.

There are two types of cell receptors for acetylcholine: muscarinic and nicotinic. The present invention encompasses administration of antagonists of either type of acetylcholine receptor. In some embodiments, antagonists of nicotinic receptors are employed.

A recent publication confirms that nicotinic receptors may modulate sebum production. Li (2103). However, neither this publication nor other current reviews of the field of treating highly prevalent diseases such as acne, where excess sebum production is well known to be a key part of disease pathogenesis (See Zanglein (2008), Kurokawa (2009), Bellew (2011), and Fulton (2013)), specifically teach or suggest use of acetylcholine receptor antagonists. Without wishing to be bound by any particular theory, we propose that at least one reason that researchers and/or reviewers might not have previously suggested such strategies is due to the above-noted understanding that such agents as nicotinic receptor antagonists cause significant skin damage. The present disclosure provides the surprising teaching that an antagonist of the nicotinic acetylcholine receptor can be used to treat skin conditions without such significant skin damage.

The skin damage known to be caused by nicotinic acetylcholine receptor antagonists, previously thought to render them unsuitable for use as agents to treat skin conditions, includes, for example, acantholysis. Please see Kurzen (2006). Acantholysis is the separation of individual epidermal keratinocytes from their neighbor, as in conditions such as pemphigus *vulgaris*. It is also described as the loss of intercellular connections, such as desmosomes, resulting in loss of cohesion between keratinocytes, again as seen in diseases such as pemphigus *vulgaris*. Clinical presentations of acantholysis include but are not limited to the appearance of blisters, pruritic eruptions, papules, acneiform lesions, vesicles, pustules, and/or bullous lesions. As well, it has been well established that certain devastating skin diseases, such as pemphigus *vulgaris,* are mediated by the destruction of nicotinic acetylcholine receptors by autoantibodies. Please see Kurzen (2006). Thus, prior to the present disclosure, it was well established that antagonizing or destroying these receptors is expected to result in extreme skin damage and pathology, and that agents that antagonize or destroy such receptors are expected to be unsuitable for use an agent treat skin conditions. The present invention discloses that use of such agents to treat skin conditions can be achieved without significant skin damage and/or signs of acantholysis and/or cell death.

The present invention is based on the discovery that nicotinic acetylcholine receptor pharmacologic antagonists can surprisingly be used safely to treat skin because it was determined that there can be a level nicotinic acetylcholine receptor antagonists that will treat, improve and/or prevent unwanted skin conditions without causing skin damage such as due to acantholysis (e.g., without causing one or more of the clinical presentations associated with acantholysis). The present invention is based on newly discovered and surprising understandings of how highly dis-regulated or diseased skin cells respond differently to pharmacologic agents impacting acetylcholine-mediated skin conditions than healthy or mildly dis-regulated or diseased skin cells.

Current belief in the field of dermatology is that patients with skin conditions such as acne respond to a given treatment at a given dose proportionately to the severity of their illness. For example, if hypothetical Patient A has 100 acne lesions on her face and hypothetical Patient B has 50 lesions on her face and they each receive a 50 mg pill of Agent X that has been shown to be an effective treatment for acne, then if Patient A has 50% reduction in the number of acne lesions (which in her case would be a reduction by 50 lesions) it would be expected that Patient B would have approximately a 50% reduction in acne lesions (which in her case would a reduction by 25 lesions). This assumption enables the comparison of patients within a study despite different patients being enrolled in the study with different levels of baseline disease severity. This assumption essentially "normalizes" changes in disease state due to treatment by reference to each patient's own baseline of disease. This assumption not only enables the comparison of patients within a study despite different patients being enrolled in the study with different levels of baseline disease severity, but it also enables the comparison of results across studies of similar (e.g., one retinoid cream versus another) or different treatments (e.g., a retinoid cream versus an antibiotic cream) for acne. The different treatments can be compared across studies by comparing the percent reductions in acne lesions for each treatment/study. See Webster (2011) who summarizes dozens of standard acne treatment clinical studies that use percent reductions in acne lesions as study outcome measures; Webster then compares these study results against one another using this same percent reduction in acne lesions for differing treatments.

An analysis of clinical study data by the inventor finds that the fundamental assumption made about the proportionality of pharmacologic response is incorrect. The clinical trial generating this data studied the effect of a topical *botulinum* treatment on acne. Acne lesion counts were made by the investigator at baseline prior to treatment and then after treatment. Please see FIGS. 1-2, which demonstrate that the greater the baseline disease severity that a patient had, the disproportionately greater response to treatment that a patient had, although all patients received the same dose of drug. In fact, the percent reduction in lesion count was highly correlated to baseline disease severity as noted in the FIGS. 1-2 week over week that the patients were observed. Thus, in the example above, Patient A might actually be observed to have 75% reduction in acne lesions, while Patient B might actually be observed to have 50% reduction in acne lesions. The implications of these unexpected and surprising findings are that patients having more diseased states (e.g., severe) would respond to a much greater extent than subjects who have less diseased states (e.g., mild). Since disease covers a spectrum, the far end of one spectrum is no disease, going to mild, then moderate, and finally severe disease. Thus, a drug dose that is toxic to skin at a high dose by mechanism "X" (e.g., acantholysis) may have no effect on skin at a low dose. In turn, because the severely diseased skin (e.g., acne) caused by mechanism "Y" (hypersebum production) is so dysregulated it is hypersensitive to this low dose through action at this dysregulated mechanism and is, in fact, therapeutic. While therapeutic in treating the acne, the drug does not cause acantholysis in the rest of the skin.

Thus, unexpectedly and surprisingly, it was found that there could be a dose of an antinicotinic acetylcholine antagonist that could effectively treat a skin condition without causing clinically observable lesions caused by acantholysis and skin cell death.

The invention provides the use of substances that antagonize acetylcholine receptors at a level that will effectively treat, improve or prevent skin conditions without otherwise causing clinically visible lesions due to acantholysis. Such substances may primarily be an antagonist of nicotinic acetylcholine receptors or may primarily affect a different receptor but secondarily be an antagonist of acetylcholine receptors due to cross-reactivity of the substance to such receptors. Skin conditions may include, but are not limited to, such skin conditions as acne (in all its forms including acne *vulgaris*), excess sebum production, seborrhea, sebaceous hyperplasia, seborrhoeic dermatitis, sebaceous adenoma, sebaceous carcinoma, sebaceous cyst, oily skin, enlarged skin pores, lichen simplex, psoriasis, rosacea, lupus, scleroderma, Raynaud's syndrome, pruritus, vitiligo, hair loss, wrinkles, or atopic dermatitis.

Appropriate acetylcholine receptor antagonists for use in accordance with the present invention will be apparent to those skilled in the art, reading the present disclosure, and include, for example, any of atracurium besylate, benztropine, biperiden, caramiphen, chlorisondamine, decamethonium bromide, dextromethorphan, dextrorphan, doxacurium, ethopropazine, hexamethonium, mecamylamine, memantine, methylcaconitine, metocurine iodide, mivacurium chloride, panchronium bromide, pipecuronium, procyclidine, quinolizidine, rocuronium bromide, succinylcholine chloride, temchine, tempoxime hydrochloride, tetracaine, trihexyphenidyl, trimethaphan, tubocurarine, or vecuronium bromide, or combinations thereof. Appropriate formulations (e.g., topical formulations) of acetylcholine receptor antagonists for use in accordance with the present invention will be apparent to those skilled in the art reading the present disclosure. In many embodiments, useful topical formulations are between 10% and 0.0009% by weight the active ingredient or specifically 5%, 3%, 2%, 1%, 0.5%, 0.1%, 0.05%, 0.01%, or 0.001% by weight.

Equivalents and Scope

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. For example, it is to be understood that any of the compositions of the invention can be used for inhibiting the formation, progression, and/or recurrence of adhesions at any of the locations, and/or due to any of the causes discussed herein or known in the art. It is also to be understood that any of the compositions made according to the methods for preparing compositions disclosed herein can be used for inhibiting the formation, progression, and/or recurrence of adhesions at any of the locations, and/or due to any of the causes discussed herein or known in the art. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects is excluded are not set forth explicitly herein.

I claim:

1. A method of treating a skin condition, the method comprising a step of:
administering to a subject suffering from or susceptible to a skin condition a substance that antagonizes acetylcholine receptors, wherein the substance that antagonizes acetylcholine receptors is selected from the group consisting of benztropine, biperiden, caramiphen, chlorisondamine, decamethonium bromide, ethopropazine, gantacurium, hexamethonium, mecamylamine, memantine, methyllycaconitine, metocurine iodide, mivacurium chloride, panchronium bromide, pipecuronium, procyclidine, quinolizidine, rocuronium bromide, succinylcholine chloride, temchine, tempoxime hydrochloride, tubocurarine, and vecuronium bromide.

2. The method of claim 1, wherein the skin condition is selected from the group consisting of acne (in all its forms including acne *vulgaris*), excess sebum production, seborrhea, sebaceous hyperplasia, seborrheic dermatitis, sebaceous adenoma, sebaceous carcinoma, sebaceous cyst, wrinkles, oily skin, or enlarged skin pores.

3. The method of claim 2, wherein the step of administering does not cause clinically visible skin lesions due to acantholysis in a majority of treated patients.

4. The method of claim 3, wherein the acetylcholine receptors are nicotinic receptors.

5. The method of claim 1, wherein the step of administering treats the skin condition.

6. The method of claim 1, wherein the step of administering improves the skin condition.

7. The method of claim 1, wherein the step of administering is performed prior to appearance of one or more features of the skin condition on the subject.

8. The method of claim 7, wherein the step of administering delays onset of or reduces severity or frequency of the one or more features of the skin condition.

9. The method of claim 1, wherein the step of administering comprises a route of administration selected from the group consisting of topical, injected, oral and transmucosal administration.

10. The method of claim 1, wherein the step of administering comprises administering a composition that is formulated as a topical pharmaceutical composition, injectable pharmaceutical composition, transmucosal pharmaceutical composition, oral pharmaceutical composition, or cosmetic.

11. A method of administering a substance that antagonizes acetylcholine receptors to a subject suffering from a condition selected from the group consisting of lichen simplex, psoriasis, rosacea, lupus, scleroderma, Raynaud's syndrome, pruritus, vitiligo, hair loss, wrinkles, and atopic dermatitis, and wherein the substance that antagonizes acetylcholine receptors is selected from the group consisting of benztropine, biperiden, caramiphen, chlorisondamine, decamethonium bromide, ethopropazine, gantacurium, hexamethonium, mecamylamine, memantine, methyllycaconitine, metocurine iodide, mivacurium chloride, panchronium bromide, pipecuronium, procyclidine, quinolizidine, rocuronium bromide, succinylcholine chloride, temchine, tempoxime hydrochloride, tubocurarine, and vecuronium bromide.

12. The method of claim 11, wherein the step of administering does not cause clinically visible skin lesions due to acantholysis in a majority of treated patients.

13. The method of claim 11, wherein the acetylcholine receptors are nicotinic receptors.

14. The method of claim 11, wherein the step of administering treats the condition.

15. The method of claim 11, wherein the step of administering improves the condition.

16. The method of claim 11, wherein the step of administering improves the appearance of the condition.

17. The method of claim 11, wherein the step of administering is performed prior to appearance of one or more features of the condition in the subject.

18. The method of claim 17, wherein the step of administering delays onset of or reduces severity or frequency of the one or more features of the condition.

19. The method of claim 11, wherein the step of administering comprises a route of administration selected from the group consisting of topical, injected, oral and transmucosal administration.

20. The method of claim 11, wherein the step of administering comprises administering a composition that is formulated as a topical pharmaceutical composition, injectable pharmaceutical composition, transmucosal pharmaceutical composition, oral pharmaceutical composition, or cosmetic.

21. The method of claim 10 or 20, wherein the topical pharmaceutical composition comprises a lotion, cream, gel, liniment, wipe or pad.

22. The method of claim 10 or 20, wherein the cosmetic comprises a lotion, cream, gel, serum, sunscreen, moisturizer, wipe, pad or foundation.

23. A topical pharmaceutical composition comprising an active ingredient comprising benztropine, biperiden, caramiphen, chlorisondamine, decamethonium bromide, ethopropazine, hexamethonium, mecamylamine, memantine, methyllycaconitine, metocurine iodide, mivacurium chloride, panchronium bromide, pipecuronium, procyclidine, quinolizidine, rocuronium bromide, succinylcholine chloride, temchine, tempoxime hydrochloride, tubocurarine, vecuronium bromide, or combinations thereof, wherein the composition is formulated so that administration of the topical pharmaceutical composition to the skin of a subject has been established not to cause clinically visible skin lesions due to acantholysis in a majority of treated patients.

24. The topical pharmaceutical composition of claim 23, wherein the composition comprises a percentage by weight of the active ingredient between 20% and 0.0009%.

25. The composition of claim 24 wherein the percentage by weight of the active ingredient is 10%, 5%, 3%, 2%, 1%, 0.5%, 0.1%, 0.05%, 0.01%, or 0.001%.

* * * * *